(12) United States Patent
Miller

(10) Patent No.: US 7,310,999 B2
(45) Date of Patent: Dec. 25, 2007

(54) BODY VOLUME MEASUREMENT APPARATUS AND METHOD OF MEASURING THE BODY VOLUME OF A PERSON

(76) Inventor: Greg Miller, 2305 Delavare Dr., St. Charles, MO (US) 63303

( * ) Notice: Subject to any disclaimer, the term of this patent is extended or adjusted under 35 U.S.C. 154(b) by 112 days.

(21) Appl. No.: 11/228,063

(22) Filed: Sep. 16, 2005

(65) Prior Publication Data

US 2007/0062269 A1    Mar. 22, 2007

(51) Int. Cl.
*G01F 17/00* (2006.01)
*B63C 11/04* (2006.01)

(52) U.S. Cl. .............................. 73/149; 2/2.15; 2/456; 128/205.26

(58) Field of Classification Search .................. 73/149; 2/456–458, 2.11–2.17; 128/200.26, 200.12, 128/205.26
See application file for complete search history.

(56) References Cited

U.S. PATENT DOCUMENTS

| 1,901,687 | A |   | 3/1933  | Zook          |
|-----------|---|---|---------|---------------|
| 3,024,465 | A | * | 3/1962  | Bould ............... 2/2.15 |
| 3,089,482 | A | * | 5/1963  | Gray ............... 600/19  |
| 3,113,448 | A |   | 12/1963 | Hardway, Jr.  |
| 3,769,834 | A |   | 11/1973 | Fletcher      |
| 4,062,079 | A |   | 12/1977 | Potter        |
| 4,112,738 | A |   | 9/1978  | Turner        |
| 4,144,749 | A |   | 3/1979  | Whitmore      |
| 4,154,098 | A |   | 5/1979  | Pelletier     |
| 4,184,371 | A |   | 1/1980  | Brachet       |
| 4,186,608 | A |   | 2/1980  | Stanonis      |
| 4,287,760 | A |   | 9/1981  | Kubo          |

(Continued)

FOREIGN PATENT DOCUMENTS

EP    0029841    7/1983

(Continued)

OTHER PUBLICATIONS

Body Composition Analysis-The Gold Standard, http://www.bodyfattest.com/ComparitiveMethodology.htm Math and Science Mentoring, http://www.sedl.org/scimast/mentoring/answers/58.html.

(Continued)

*Primary Examiner*—Hezron Williams
*Assistant Examiner*—David A. Rogers
(74) *Attorney, Agent, or Firm*—Polster Lieder Woodruff & Lucchesi, L.C.

(57) ABSTRACT

An apparatus and method for measuring a volume of a person's body. The apparatus comprises a body suit having an inner layer and an outer layer which forms a body portion and a head portion. The body suit further has a cavity defined within the inner layer, the cavity having an amount of known initial volume. The apparatus further comprises a fluid assembly which is removeably connected to the body suit. The fluid assembly is configured to discharge fluid into the cavity and around the body when the body is disposed within the cavity. The fluid assembly discharges the fluid to fill the cavity from a first position to a second position, the second position having an amount of a final volume such that a difference between the known initial volume amount and the final volume amount of the second position equals the volume of the body.

15 Claims, 6 Drawing Sheets

U.S. PATENT DOCUMENTS

| | | | |
|---|---|---|---|
| 4,294,242 A * | 10/1981 | Cowans | 128/201.13 |
| 4,369,652 A | 1/1983 | Gundlach | |
| 4,533,335 A | 8/1985 | Hoshino | |
| 4,753,307 A | 6/1988 | Muehlenbein | |
| 4,841,982 A * | 6/1989 | Nikiforov et al. | 600/529 |
| 4,873,866 A | 10/1989 | Fairbanks | |
| 4,888,718 A | 12/1989 | Furuse | |
| 5,052,405 A | 10/1991 | Batchelder | |
| 5,105,825 A | 4/1992 | Dempster | |
| 5,127,896 A * | 7/1992 | de Gaston | 600/20 |
| 5,379,777 A * | 1/1995 | Lomask | 600/529 |
| 5,421,326 A | 6/1995 | Rankin et al. | |
| 5,450,750 A | 9/1995 | Abler | |
| 5,595,189 A | 1/1997 | Naim | |
| 5,620,005 A | 4/1997 | Ganshor | |
| 5,680,871 A | 10/1997 | Ganshorn | |
| 5,860,162 A | 1/1999 | Love | |
| 5,948,977 A | 9/1999 | Siconolfi | |
| 6,345,195 B1 | 2/2002 | Herskowits | |
| 6,778,926 B2 | 8/2004 | Dempster | |
| 6,829,927 B2 | 12/2004 | Retterath | |
| 6,910,373 B2 * | 6/2005 | Dempster et al. | 73/149 |
| 6,927,858 B2 * | 8/2005 | Boone et al. | 356/437 |

FOREIGN PATENT DOCUMENTS

| | | |
|---|---|---|
| FR | 1480470 | 5/1967 |
| GB | 2220752 | 1/1990 |
| GB | 2344183 | 5/2000 |
| JP | 02170018 | 6/1990 |
| JP | 2004305653 | 11/2004 |
| WO | WO 9000032 A1 * | 1/1990 |
| WO | WO 9200700 A * | 1/1992 |
| WO | WO 9324821 A1 * | 12/1993 |
| WO | WO 9835612 A1 * | 8/1998 |
| WO | WO 0101354 A1 * | 1/2001 |
| WO | WO 0123828 A2 * | 4/2001 |
| WO | WO 03058175 A2 * | 7/2003 |
| WO | WO 2004069321 A1 * | 8/2004 |

OTHER PUBLICATIONS

Body Composition: How Should It Be Measured? Does It Affect Sport Performance? SSE#52-vol. 7 (1994), No. 5, http://www.gssiweb.com.

Retrospectroscope, The Body Plethysmograph (Body Box) http:www.thoracic.org/aboutats/retrospectroscope/adobe/31-Man-CansConclusion.pdf.

* cited by examiner

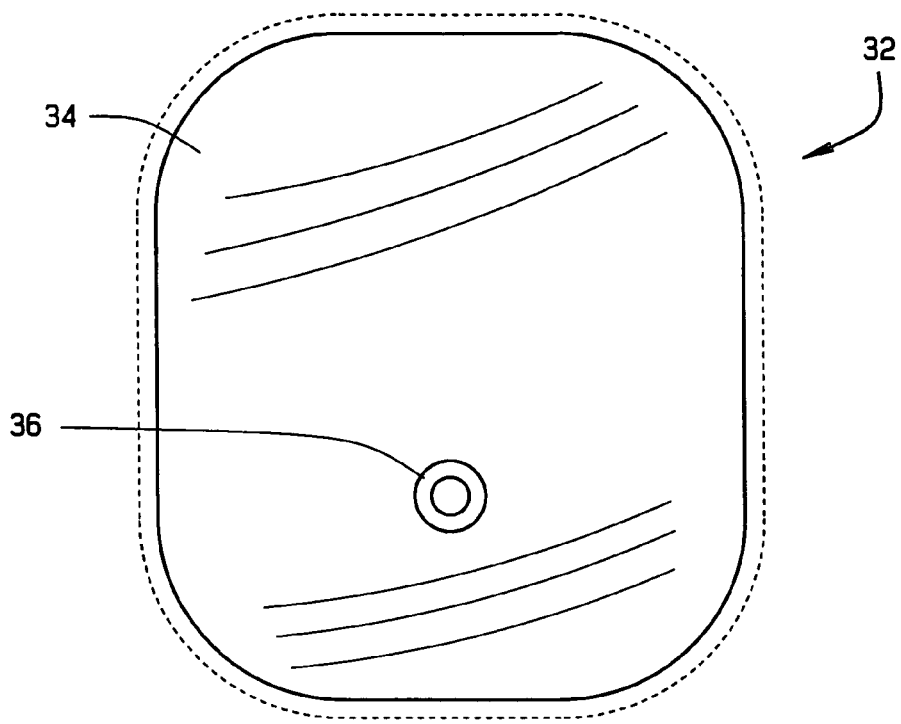
FIG. 2
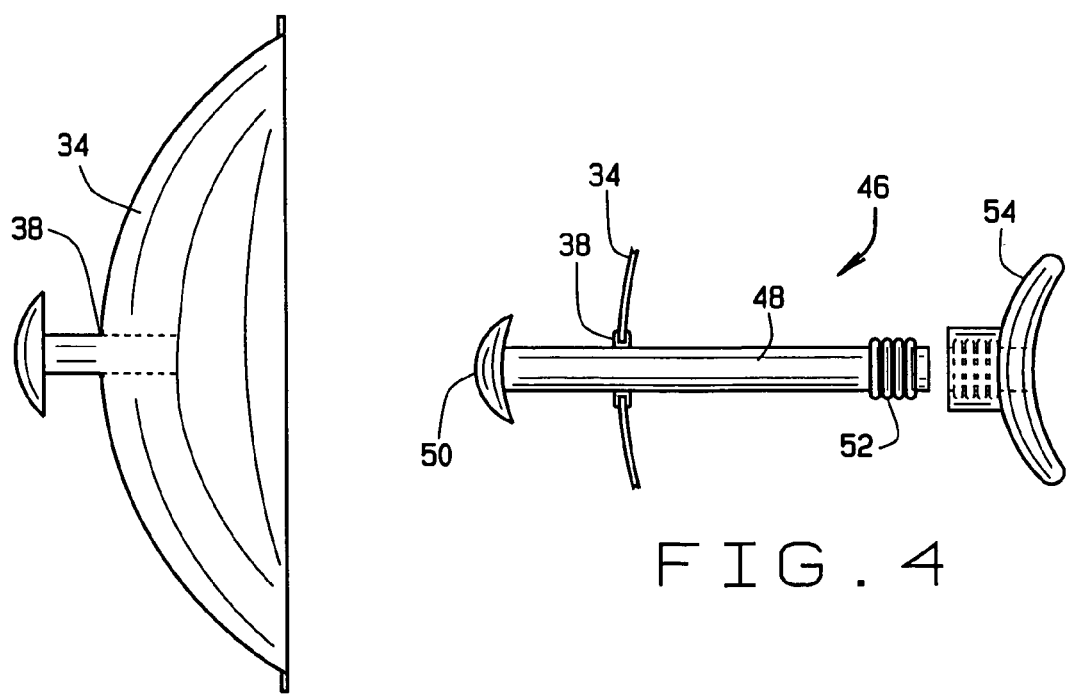
FIG. 3
FIG. 4

BODY VOLUME MEASUREMENT APPARATUS AND METHOD OF MEASURING THE BODY VOLUME OF A PERSON

CROSS-REFERENCE TO RELATED APPLICATIONS

Not Applicable.

STATEMENT REGARDING FEDERALLY SPONSORED RESEARCH

Not Applicable.

BACKGROUND OF THE DISCLOSURE

The present disclosure relates to an apparatus that measures the body volume of a person, and in particular, to a body suit and a fluid assembly that discharges fluid into the body suit while the person is wearing the suit to measure the amount of fluid the person displaces in a fixed area.

Body composition is the technical term used to describe the different components that, when taken together, makes up a person's body weight. When analyzing body composition it is often convenient to think of the body as made of two components: fat and non-fat. The non-fat portion is usually called "fat free mass" or "lean body mass".

The human body is composed of a variety of different tissue types. The so-called 'lean' tissues, such as muscle, bone and organs are metabolically active, while adipose, or fat tissue is not. Scientists divide adipose tissue into three different categories: 1. Essential fat, which supports life, and is extremely important to normal bodily function; 2. Storage fat, which protects internal organs and supplies some energy requirements and 3. Non-essential fat, which serves no real purpose and may be detrimental to health The difference in these tissues is not readily distinguishable by stepping on a scale. A scale simply takes the sum of everything (fat, muscle, water, hair, etc.) and gives an absolute weight measurement. Scales can't determine the lean-to-fat ratio of that weight. A person can be "overweight" and not "over-fat". A bodybuilder, for example, may have 8% body fat, yet at two hundred and fifty pounds may be considered "over-weight" by a typical height-weight chart. Therefore, these charts are not a good indication of a person's ideal body weight for optimal health, much less for athletic performance.

The most common body fat test uses the skinfolder caliper, a device that pinches the person's skin, pulling fat away from muscles and bones. Typically, the tester pinches three of four different sites on the body, such as the abdomen, arm, and back. The tester enters the thickness of each pinch into a formula to determine the subcutaneous body fat level.

The tester, however, may not pinch exactly the right spot, or may not pull all the fat away from the muscle. Or the tester may pinch too hard and accidentally pull some of the muscle. The calipers must exert a standard pressure and measure thickness to very small levels. As such, tests can vary greatly from tester to tester. Also, research shows that certain formulas are more accurate for certain ethnic groups, age ranges, and fitness levels.

Underwater weighing is an accurate but cumbersome and expensive method of body fat testing. In this method, the person sits on a scale in a tank of warm water, blows the air out of the lungs and bends forward until the person is completely submerged. The person remains submerged for a few seconds while an underwater weight registers on a high precision scale. The result is then entered into a mathematical equation. This test is repeated and the best results are averaged to get an accurate reading of the amount of fat in the person. This costly method however is not efficient for the person due to anxiety, discomfort on being submerged, and pre-test guidelines.

Still further, the Body Mass Index is often used to quantify a person's obesity level. This is simple test relates to a formula of the person's height squared, divided by the person's weight. The result is looked up on a table. Only a person's height and weight are used and no indication of actual lean or fat mass can be determined. As such, this test does not take not body composition information into account, and is simply an average based on population studies.

BRIEF SUMMARY OF THE DISCLOSURE

Briefly stated, the present disclosure provides an apparatus for measuring a volume of a person's body. The apparatus comprises a body suit having an inner layer and an outer layer which forms a body portion and a head portion. The body suit further has a cavity defined within the inner layer, the cavity having an amount of known initial volume determined by known means.

The apparatus also comprises a mask assembly sealably integrated with the head portion, wherein the mask assembly includes a faceplate having an aperture defined therethrough and includes a breathing tube which is removeably inserted within the aperture.

The apparatus further comprises a fluid assembly which is removeably connected to the body suit. The fluid assembly is configured to discharge fluid into the cavity and around the body when the body is disposed within the cavity. The fluid assembly discharges the fluid to fill the cavity from a first position to a second position, the second position having an amount of a final volume such that a difference between the known initial volume amount and the final volume amount of the second position equals the volume of the body.

The present disclosure provides a method of measuring a volume of a person's body which is disposed within a body suit having an inner layer and an outer layer. The method comprises determining an amount of volume of a cavity of the body suit. Next the body is disposed within the cavity such that the inner layer contacts the body in a first position. Once the body is disposed within the body suit, a fluid assembly connects to the body suit.

The fluid assembly discharges into the cavity and in contact with the body in order to fill the cavity to a second position having a final amount of volume. Then a difference between the determined volume amount of the cavity and the final volume amount of the cavity is calculated to obtain a measured amount of fluid discharged into the cavity.

The foregoing and other objects, features, and advantages of the disclosure as well as presently preferred embodiments thereof will become more apparent from the reading of the following description in connection with the accompanying drawings.

BRIEF DESCRIPTION OF THE SEVERAL VIEWS OF THE DRAWINGS

In the accompanying drawings which form part of the specification:

FIG. 2 is a front elevational view of a mask of the body suit constructed in accordance with and embodying the present disclosure;

FIG. 3 is a side elevational view of the mask of FIG. 2 illustrating a breathing tube disposed within the mask;

FIG. 4 is a breakaway view of the breathing tube of FIG. 3 illustrating components of the breathing tube;

Corresponding reference numerals indicate corresponding parts throughout the several figures of the drawings.

DESCRIPTION OF THE PREFERRED EMBODIMENT

The following detailed description illustrates the disclosure by way of example and not by way of limitation. The description clearly enables one skilled in the art to make and use the disclosure, describes several embodiments, adaptations, variations, alternatives, and uses of the disclosure, including what is presently believed to be the best mode of carrying out the disclosure.

As noted, the Body Mass Index is a widely used method of determining whether a person is overweight or within their 'healthy target' range. However, it doesn't take into account a person's body composition. A body builder, for his height, when compared to the general population may register as overweight, but his actual body fat percentage may be well within the healthy limits.

Fat weighs less than muscle. Fat and muscle each displace a known amount of water, i.e., they have a known volume. If you know how much someone weighs, then you can determine how much water they would displace if they were all muscle. Compare that to how much water they actually displace, and you can figure out how much of their body composition is fat, and not muscle.

The only way to get a true measurement of a person's obesity level is to take into account the person's body composition. In order to do this, the person's body volume must be measured. By dividing the person's body weight by the cubic inches of their body volume, body density, lean body mass, and body fat percentage can be accurately calculated using standard equations.

Figure 1:
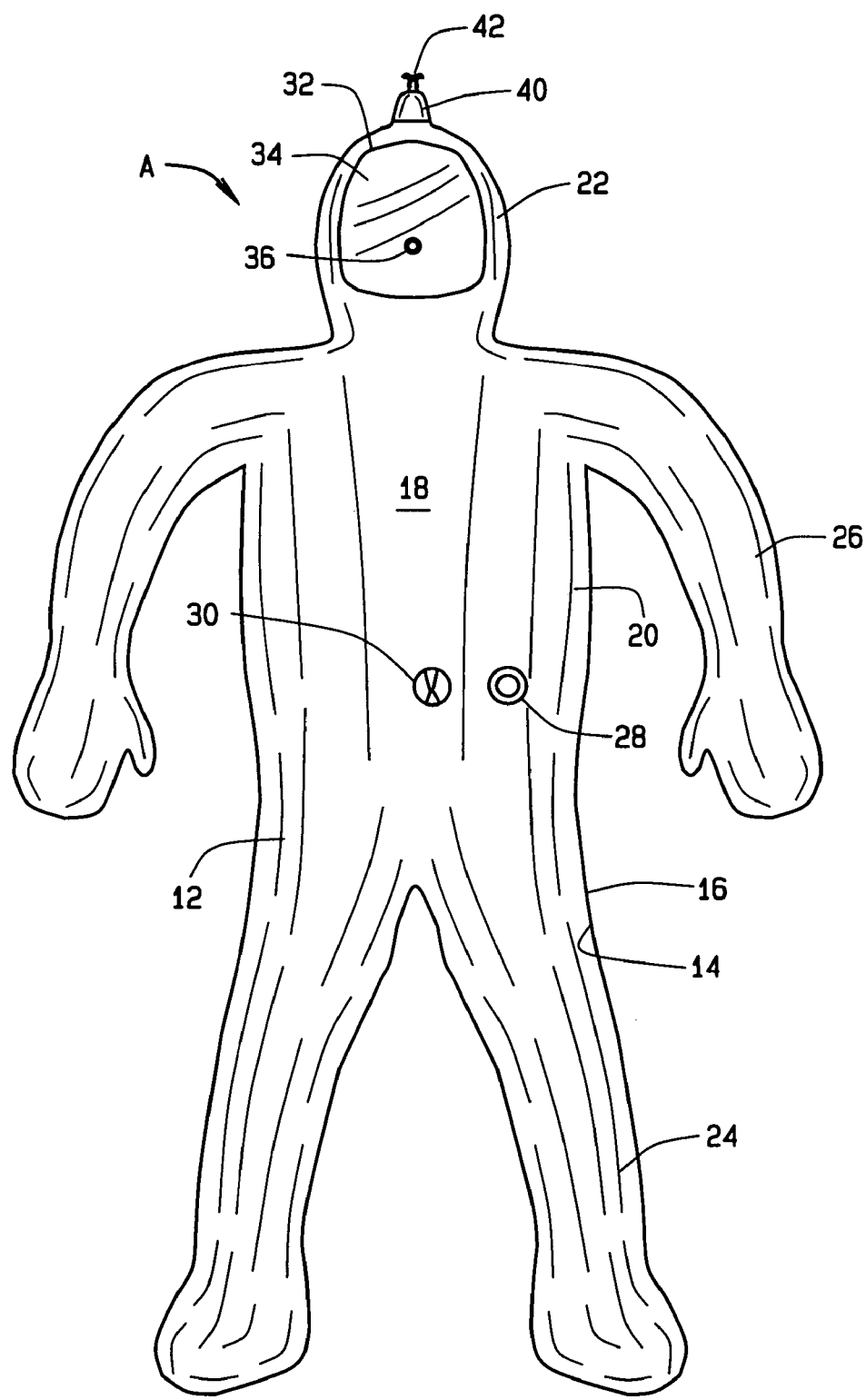
FIG. 1 is a front elevational view of the volume measurement apparatus illustrating an inner layer and an outer layer of a body suit constructed in accordance with and embodying the present disclosure.

Referring to the drawings, an apparatus A for measuring a volume of a person's body 10 (FIG. 6) comprises a one-piece body suit 12 (FIG. 1). The body suit 12 comprises various sizes depending on the height of the person being measured. As such, size would vary by height, but each size would be large enough to accommodate a wide range of body types for the particular height and manufactured to exact specification to ensure an accurate, repeatable volume capacity when empty. The body suit 12 includes an inner layer 14 and an outer layer 16. The inner layer 14 defines a cavity 18 wherein the cavity 18 has a known initial volume amount. The layers 14, 16 form a body portion 20, a head portion 22, legs portion and arms portion. The body portion 20 includes a fluid fill connector 28 in the form of a male threaded coupling. The body portion 20 further includes a drain connector 30 in the form of a threaded coupling. In one embodiment, a drain valve connects with the drain connector 30.

As shown, the head portion 22 includes a mask assembly 32 which sealably integrates with the head portion 22. The mask assembly 32 has a faceplate 34 with an aperture 36 defined therethrough. The faceplate 34 comprises a clear acrylic material where the aperture 36 includes a seal 38 such as an elastomer O-ring. The head portion 22 further includes a visual fill indicator 40. The visual fill indicator 40 is in fluid communication with the cavity 18 as will be discussed. Additionally, the head portion 22 includes a relief valve 42, such as a check valve, positioned above the visual fill indicator 40.

Turning to FIGS. 2-4, components of the mask assembly 32 are shown. FIG. 3 illustrates a breathing assembly 46 associated with the faceplate 34 (FIG. 2). The breathing assembly 46 comprises a breathing tube 48 and a mouthpiece 54. The breathing tube 48 has a breathing aperture 36 at one end and a tube connector 52 at the opposite end. The breathing tube 48 removeably inserts within the aperture 36 of the faceplate 34. The tube connector 52 removably attaches to the disposable mouthpiece 54, wherein the tube connector 52 acts as a stop to keep the breathing tube 48 positioned within the aperture 36. As shown in FIG. 4, the breathing tube 48 positions the breathing aperture 36 beyond the outer surface of the faceplate 34.

Figure 5:
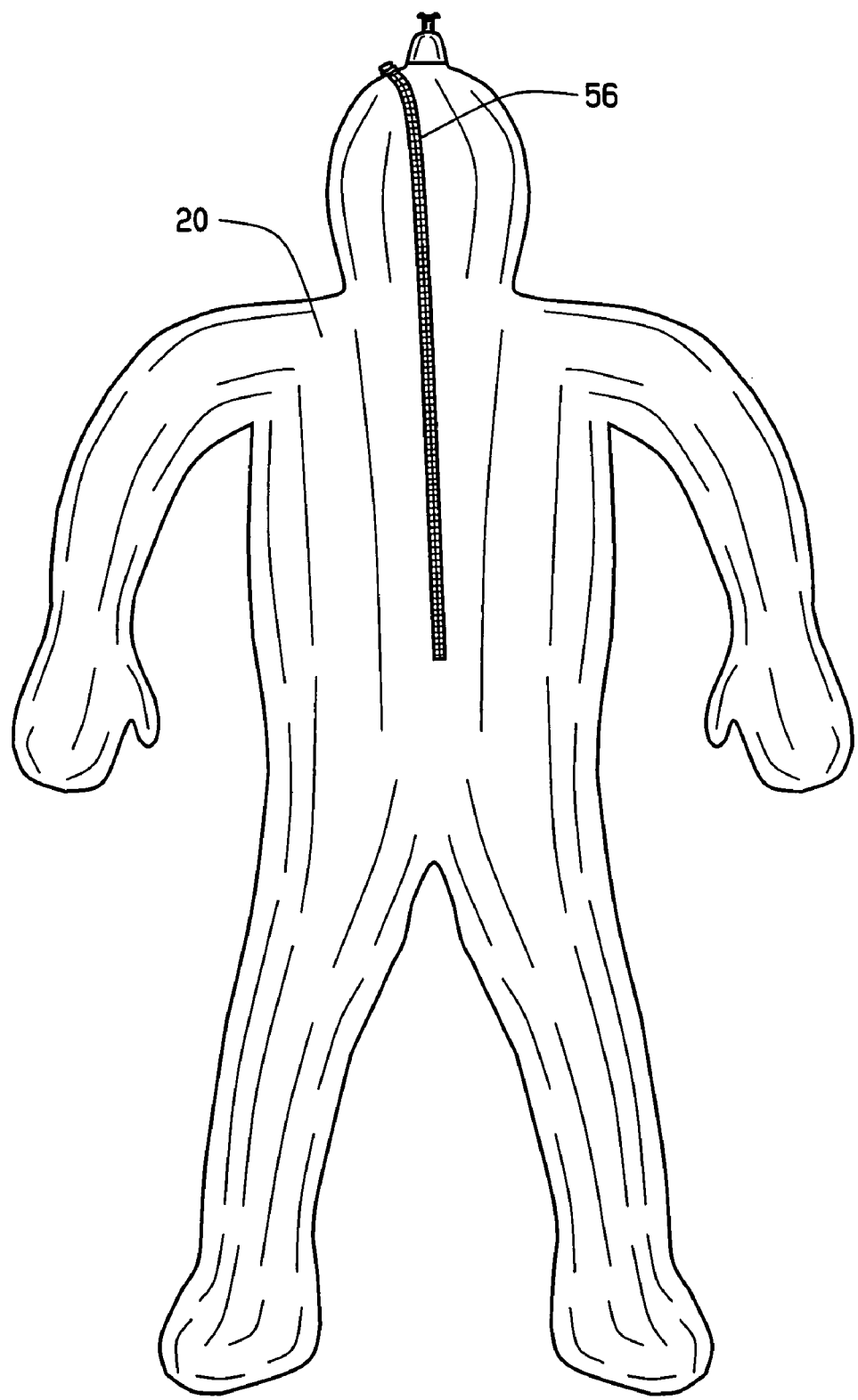
FIG. 5 is a back elevational view of the volume measurement apparatus of FIG. 1 illustrating a removable fastener constructed in accordance with and embodying the present disclosure.
Figure 6:
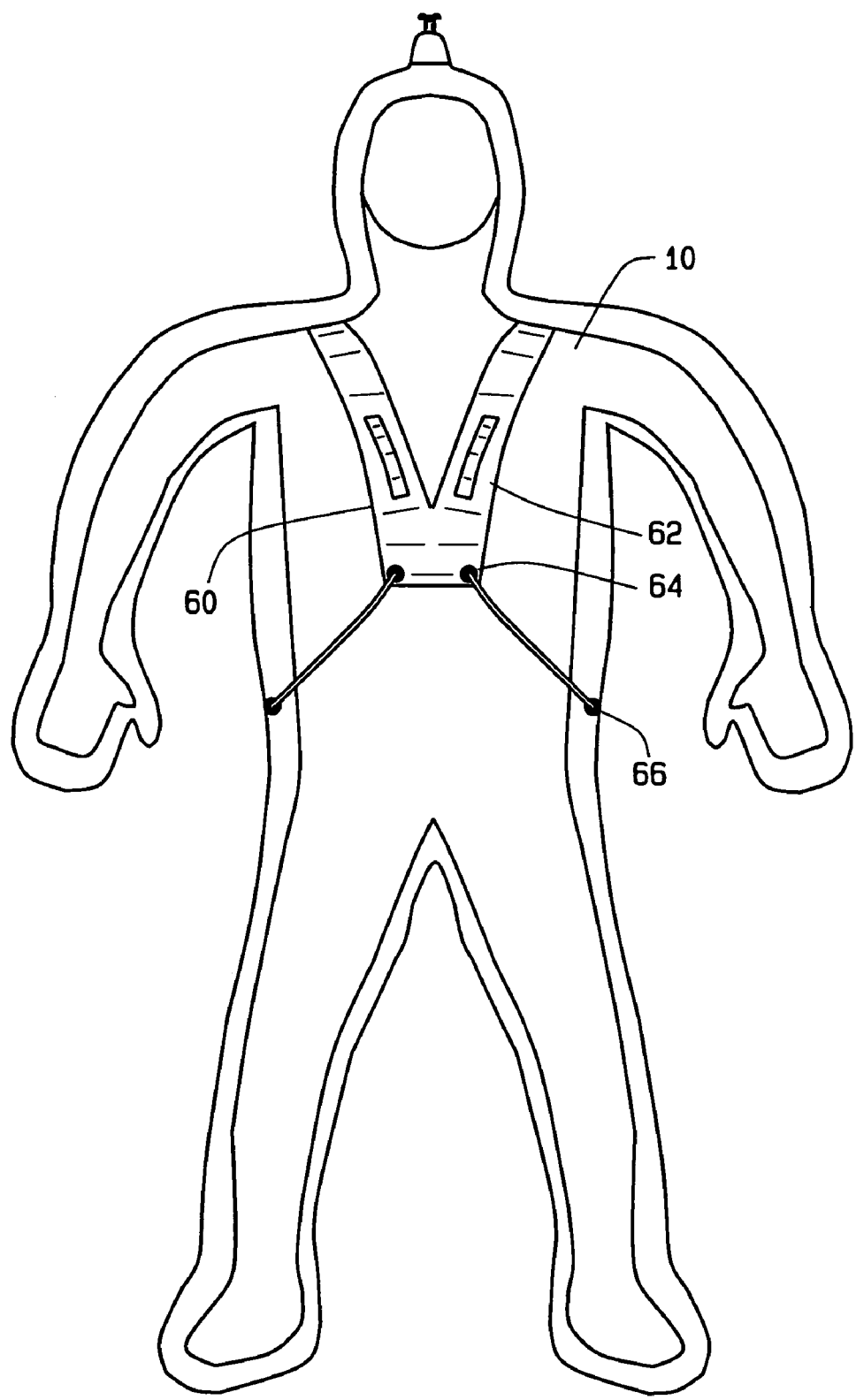
FIG. 6 is a front elevational cross sectional view of the volume measurement apparatus illustrating a shoulder harness.

Turning to FIG. 5, the body portion 20 includes a removable fastener 56 in the form of a zipper. The removable fastener 56 extends from the head portion 22 to the body portion 20. As shown in FIG. 6, the body portion 20 also includes a shoulder harness 58 which has a first pair of straps 60 and a second pair of straps 62. Each of the second pair of straps 62 includes a first end 64 and a second end 66 such that each first end 64 connects with the respective strap of the first pair of straps 60 while each second end 66 connects with the inner layer 14 of the body suit 12.

Figure 7:
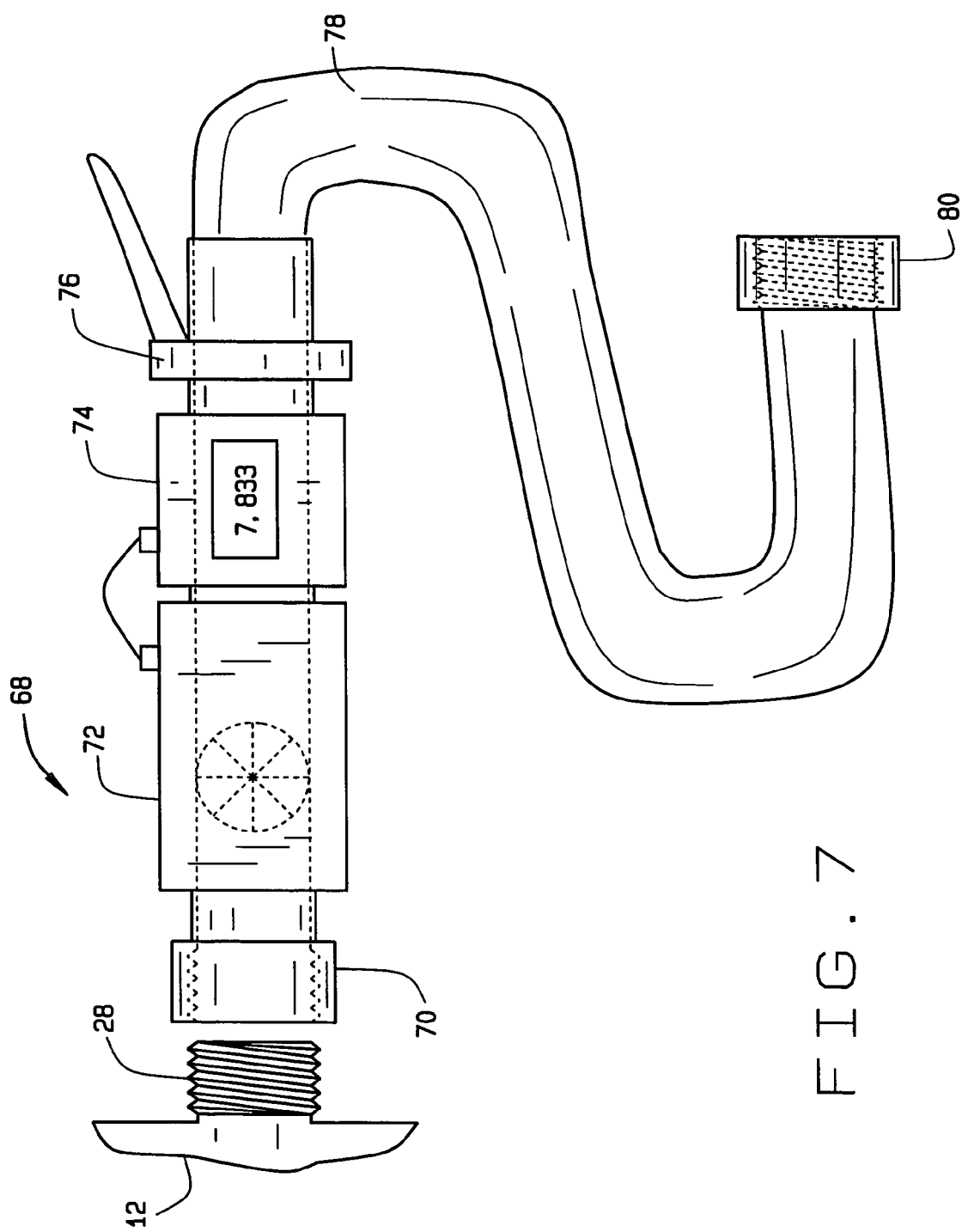
FIG. 7 is an assembly view of a fluid assembly constructed in accordance with and embodying the present disclosure.

Referring to FIG. 7, the apparatus A comprises a fluid assembly 68. The fluid assembly 68 comprises a discharge connector 70, a flow meter 72, a digital readout 74, a fill valve 76, a fill hose 78 and fill connector 80. The digital readout 74 is in communication with the flow meter 72. The fluid assembly 68 removeably connects to the body suit 12 via the fluid fill connector 28. The fluid assembly 68 also removeably connects the fluid source (not shown) such as a showerhead or sink faucet via the fill connector 80.

Figure 8:
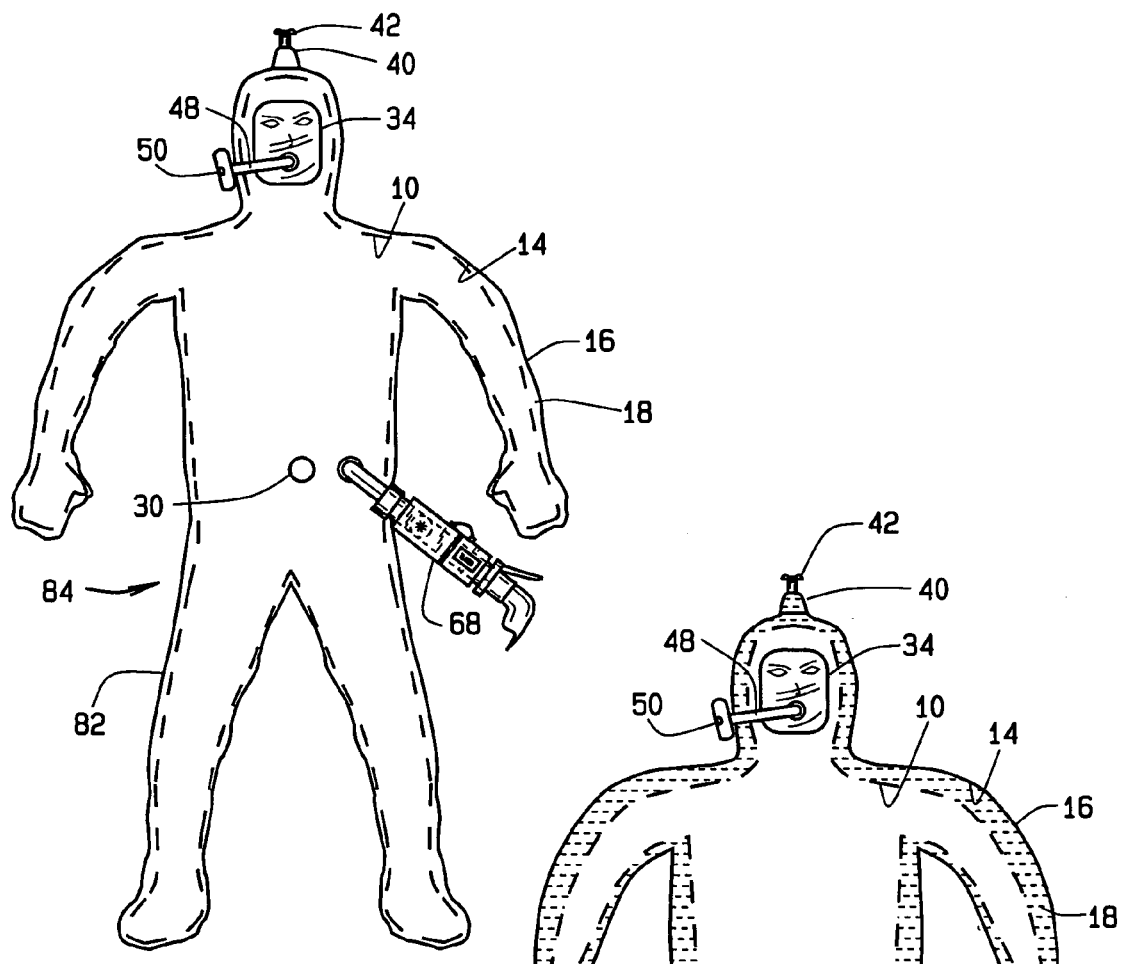
FIG. 8 is a front elevational view of the body suit in a first position illustrating the fluid assembly attached to the body suit.
Figure 9:
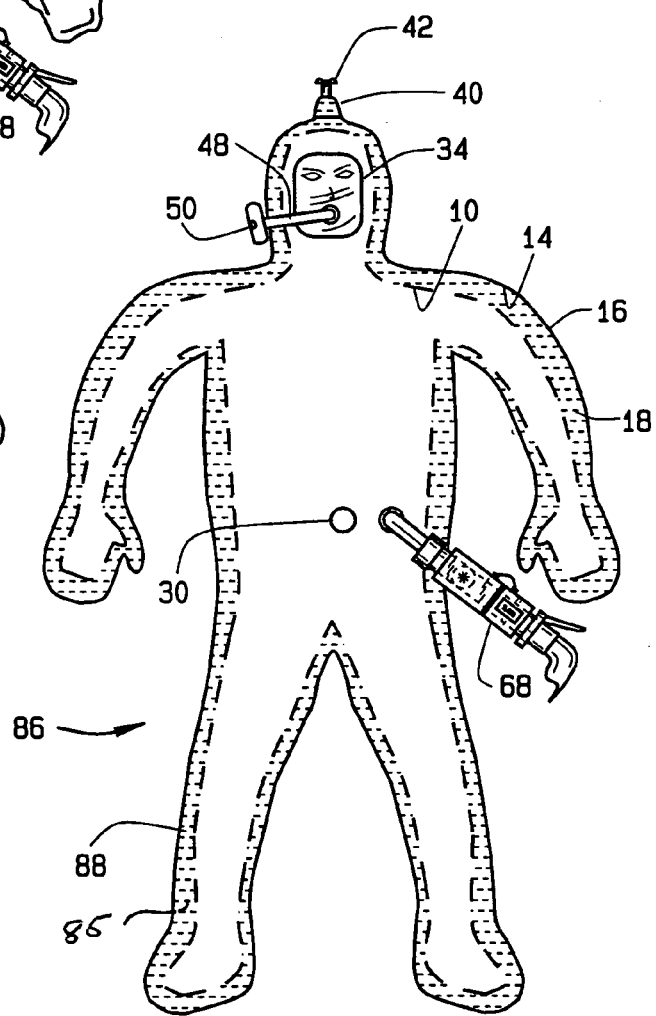
FIG. 9 is a front elevational view of the body suit in a second position illustrating discharged fluid positioned within the body suit.

Turning to FIGS. 8 and 9 and referring to FIGS. 1-7, the apparatus A of the present disclosure provides a method of measuring a person's body volume. During use, an operator determines the initial volume 82 of cavity 18 by known means, when the person is not positioned within the body suit 12. After determining the initial volume 82 of the cavity 18, the operator unfastens the removable fastener 56 and the person enters the cavity 18 to fit within the body suit 12, wherein the person is preferably only wearing a swimsuit. The breathing tube 48 inserts into the aperture 36 prior to the person entering the body suit 12. While fitting into the body suit 12, the person inserts the removable mouthpiece 54 into his/her mouth. After fitting the body portion 20, head portion 22, leg portion 24 and arm portion 26 over of the respective body parts, the operator fastens the removable fastener 56 to seal 38 the person within the body suit 12.

Once positioned inside the body suit 12, the inner layer 14 of the body suit 12 positions against and in contact with the person's body 10 in a first position 84. The operator then connects the fluid assembly 68 to the body suit 12 by connecting the discharge connector 70 to the fluid fill connector 28. The operator also plugs the drain connector 30 or closes the drain valve.

The operator then opens the fill valve 76 to discharge fluid 85, such as a liquid (i.e., water), from the fluid source (not shown) through the flow meter 72 and into the cavity 18 of the body suit 12. As such, fluid 85 flows into the cavity 18 between the person's body and the inner layer 14. The fluid 85 fills the cavity 18 from the first position 84 to a second position 86 until the second position 86 achieves an amount of a final volume 88. In the second position 86, the inner layer 14 is positioned away from the body. The shoulder harness 58 assists the person to support the weight of the fluid 85 during the fill process.

During this fluid discharge into the cavity 18, the fluid 85 contacts the person's body 10. The relief valve 42, which is in fluid communication with the cavity 18, allows air to escape during the fill process and prevents the fluid pressure from reaching an uncomfortable level. Furthermore, the visual fill indicator 40, which is also in communication with the cavity 18, allows the operator to determine when the fluid 85 has filled the cavity 18. Additionally, when the fluid 85 begins to escape from the relief valve 42, the operator becomes aware that the cavity 18 is full. Once the final volume 88 of the second position 86 is achieved and recorded by the flow meter 72 and digital readout 74, the operator shuts off the fill valve 76 and opens the drain connector 30/drain valve to drain the fluid 85 from the cavity 18.

During the fill process, the flow meter 72 measures the amount of fluid 85 discharged in the cavity 18 while the digital readout 74 provides a numerical display to the operator of the amount of discharge fluid into the cavity 18. Based on the digital readout 74 and the final volume 88 of the second position 86, the operator calculates a difference between the known initial volume 82 of a cavity 18 and the final volume amount 88 wherein this difference equals the volume of the person's body. The operator may then enter the volume of the person's body into known equations in order to calculate the body composition. Thus, by subtracting the amount of fluid needed to fill the cavity from the known initial volume 82 of the body suit 12 to the final volume 88 of the second position 86, the person's true body volume can be determined.

Each body suit 12 may be recalibrated if necessary due to elevation, fluid pressure, temperature variation, etc., by simply zipping the body suit 12 and filling it to capacity while empty, and making note of the volume needed to fill to the point where the relief valve 42 releases fluid.

During the fill process, the person may wear swim goggles and a nose plug for comfort, easily see through the acrylic face plate 34, maintain mobility within the body suit 12, and breathe easily through the sterile, flexible mouthpiece 54. The relief valve 42 on top of the body suit 12 would insure that the fluid pressure would never become uncomfortable, and insure accurate, repeatable fill pressure. Furthermore, in order to get the most accurate reading, the person would have to exhale as much as possible at the very end to get as much fluid as possible through the flow meter 72. The fluid 85 is not limited to a liquid such as water. For example, the fluid 85 may comprise air, oxygen, gas mixture, medicinal fluid and therapeutic fluid.

In view of the above, it will be seen that the several objects of the disclosure are achieved and other advantageous results are obtained. As various changes could be made in the above constructions without departing from the scope of the disclosure, it is intended that all matter contained in the above description or shown in the accompanying drawings shall be interpreted as illustrative and not in a limiting sense.

The invention claimed is:

1. An apparatus for measuring a volume of a person's body, the apparatus, comprising:

a body suit having an inner layer and an outer layer which forms a body portion and a head portion, the body suit further having a cavity defined within the inner layer and further having a closeable vent defined through the outer layer and the inner layer to allow the cavity to communicate with the atmosphere, the cavity having a known volume;

a mask assembly sealably integrated with the head portion, the mask assembly comprising a face plate having an aperture defined therethrough and comprising a breathing tube which is removeably inserted within the aperture; and a fluid assembly which is removeably connected to the body suit, the fluid assembly having a flow meter and a readout in communication with the flow meter, the fluid assembly being configured to discharge fluid into the cavity and around the body when the body is disposed within the cavity wherein the fluid assembly discharges the fluid to fill the cavity from a first position to a second position, the second position achieving the known volume wherein the flow meter measures the volume of discharged fluid entering the cavity until the cavity reaches the known final volume such that a difference, as calculated by the readout, between the known volume of the cavity and the measured volume of discharged fluid equals the volume of the person's body.

2. The apparatus of claim 1 further comprising a visual fill indicator positioned on the top of the head portion and in communication with the cavity.

3. The apparatus of claim 1 wherein the fluid comprises at least one of water, air oxygen, gas mixture, medicinal fluid and therapeutic fluid.

4. The apparatus of claim 1 further comprising a shoulder harness which includes a first pair of straps and a second pair of straps.

5. The apparatus of claim 4 wherein the first pair of straps fastens to the body disposed within the cavity.

6. The apparatus of claim 5 wherein each of the second pair of straps include a first end and a second end such that each first end connects with a respective strap of the first pair of straps and that each second end connects with the inner layer of the body suit.

7. The apparatus of claim 1 wherein the inner layer is positionable against the body in the first position.

8. The apparatus of claim 7 wherein the inner layer is positioned away from the body in the second position.

9. The apparatus of claim 8 wherein the fluid is in contact with the body in the second position.

10. A body suit for measuring a volume of a person's body when the body is disposed within the body suit, the body suit, comprising:

an inner layer and an outer layer which forms a body portion and a head portion, the inner layer is positionable against the body in a first position while the outer layer is exposed to the atmosphere, the body suit further having a cavity defined within the inner layer the cavity having a known volume, the body suit further having a closeable vent and a visual fill indicator, the closeable vent positioned on the head portion and defined through the outer layer and the inner layer to allow the cavity to communicate with the atmosphere and the visual fill indicator positioned on the head portion and defined through the outer layer and the inner layer to indicate of the cavity achieving the known volume;

a mask assembly sealably integrated with the head portion, the mask assembly comprising a face plate having an aperture defined therethrough and comprising a breathing tube which is removeably inserted within the aperture; and a fluid assembly which is removeably connected to the body suit, the fluid assembly having a flow meter and a readout in communication with the flow meter, the fluid assembly being configured to discharge fluid into the cavity and around the body when the body is disposed within the cavity wherein the fluid assembly discharges the fluid to fill the cavity from a first position to a second position, the second position achieving the known volume wherein the flow meter measures the volume of discharged fluid entering the cavity until the cavity reaches the known final volume such that a difference, as calculated by the readout, between the known volume of the cavity and the measured volume of discharged fluid equals the volume of the person's body.

11. The apparatus of claim 10 further comprising a shoulder harness which includes a pair of shoulder straps and a pair of body straps wherein the shoulder straps fasten to the body and the body straps fasten to the inner layer of the body suit.

12. The apparatus of claim 10 wherein the body portion comprises a removable fastener which is configured to allow entry of the body into the cavity.

13. A method of measuring a volume of a person's body which is disposed within a body suit having an inner layer, an outer layer and a known volume, comprising:

disposing the body within the cavity such that the inner layer contacts the body in a first position;

connecting a fluid assembly to the body suit;

discharging a fluid from the fluid assembly into the cavity and in contact with the body in order to fill the cavity to a second position achieving-the known volume wherein the inner layer is positioned away from the body in the second position;

measuring the volume of discharged fluid entering the cavity until the cavity reaches the known volume; and calculating a difference between the known volume of the cavity and the measured volume of discharged fluid into the cavity to determine the volume of the person's body.

14. The method of claim 13 wherein discharging the fluid from the fluid assembly into the cavity and in contact with the body further comprises venting the body suit as the fluid discharges into the cavity.

15. The method of claim 13 further comprising visually indicating the known volume amount of the second position.

* * * * *